United States Patent
Lloyd et al.

(10) Patent No.: US 6,754,518 B1
(45) Date of Patent: Jun. 22, 2004

(54) METHOD AND APPARATUS FOR DETECTING AN OBJECT WITHIN A DYNAMIC SCATTERING MEDIA

(75) Inventors: Christopher J. Lloyd, Manchester (GB); David J. Clarke, Sandbach (GB)

(73) Assignee: The Victoria University of Manchester, Manchester (GB)

( * ) Notice: Subject to any disclaimer, the term of this patent is extended or adjusted under 35 U.S.C. 154(b) by 0 days.

(21) Appl. No.: 09/355,012
(22) PCT Filed: Nov. 25, 1998
(86) PCT No.: PCT/GB98/03510
§ 371 (c)(1),
(2), (4) Date: Sep. 17, 1999
(87) PCT Pub. No.: WO99/27348
PCT Pub. Date: Jun. 3, 1999

(30) Foreign Application Priority Data

Nov. 25, 1997 (GB) .............................................. 9724835

(51) Int. Cl.[7] .............................................. A61B 5/00
(52) U.S. Cl. ...................... 600/407; 600/473; 600/476; 356/432; 356/433
(58) Field of Search ........................ 600/473, 475–479, 600/407, 425; 356/342, 343

(56) References Cited

U.S. PATENT DOCUMENTS

| | | |
|---|---|---|
| 3,778,614 A | 12/1973 | Hounsfield |
| 3,910,701 A | 10/1975 | Henderson et al. |
| 4,556,057 A | 12/1985 | Hiruma et al. |
| 4,823,601 A | 4/1989 | Barna |
| 4,832,035 A | 5/1989 | Cho et al. |
| 5,054,487 A | 10/1991 | Clarke |
| 5,070,455 A | 12/1991 | Singer et al. |
| 5,119,815 A | 6/1992 | Chance |
| 5,190,039 A | 3/1993 | Takeuchi et al. |
| 5,203,339 A | 4/1993 | Knuttel et al. |
| 5,353,799 A * | 10/1994 | Chance ........................ 600/473 |
| 5,416,582 A | 5/1995 | Knutson et al. |
| 5,418,797 A | 5/1995 | Bashkansky et al. |
| 5,441,053 A | 8/1995 | Lodder et al. |
| 5,528,365 A | 6/1996 | Gonatas |
| 5,606,969 A | 3/1997 | Butler et al. |
| 5,625,458 A | 4/1997 | Alfano et al. |
| 5,664,574 A | 9/1997 | Chance |
| 5,684,588 A | 11/1997 | Khoury et al. |
| 5,814,730 A | 9/1998 | Brodeur et al. |
| 5,941,827 A * | 8/1999 | Papaioannou ............... 600/473 |
| 5,983,121 A * | 11/1999 | Tsuchiya .................... 600/473 |
| 6,064,917 A * | 5/2000 | Matson ....................... 600/473 |

FOREIGN PATENT DOCUMENTS

| | | |
|---|---|---|
| DE | 4303047 A1 | 8/1994 |
| EP | 0692708 A2 | 1/1996 |
| WO | WO 93/13395 | 7/1993 |
| WO | WO 94/18545 | 8/1994 |

\* cited by examiner

Primary Examiner—Ruth S. Smith
(74) Attorney, Agent, or Firm—Nixon & Vanderhye P.C.

(57) ABSTRACT

A method of detecting an object located within a dynamic scattering media, includes i) directing a continuous coherent light wave of predetermined wavelength into the media; ii) detecting dynamically scattered light emerging from the media; iii) correlating the detected light photons in the time or frequency domain; iv) determining the presence of an object from analysis of differences between the correlation and a correlation which would arise from photons scattered by the media only; and v) determining the approximate position of the object within the media from the analysis of the correlation and knowledge of the mean transport path of the light wave of predetermined wavelength within the media.

13 Claims, 9 Drawing Sheets

METHOD AND APPARATUS FOR DETECTING AN OBJECT WITHIN A DYNAMIC SCATTERING MEDIA

BACKGROUND OF THE INVENTION

1. Field of the Invention

The present invention relates to a method and apparatus for detecting and/or imaging an object.

2. Related Art

Image through turbid media is often carried out using Time of Flight measurements. Various methods of time of flight measurement are known. The majority of these methods measure the time taken by pulses of light to travel a return path. Since the velocity of light is both constant and known for most materials, measurements of time of flight can be readily converted into images of the medium through which the light has passed.

Time of Flight imaging is particularly useful when imaging over large distances or in semi-turbid media. However, when dealing with short distances image resolution decreases rapidly, since the speed of light is so great that, for example, a spatial resolution of 1 m will require a detector with a temporal resolution of 5 ns. The shortest measurable distance and the image resolution obtainable using Time of Flight imaging is thus limited by the response time of the detectors used. A further disadvantage or Time of Flight imaging is that the reset time of the detectors used is considerably longer than the jitter time, so that the detectors are only capable of detection for a very short period of their total operating time. An alternative method of imagine through turbid media is it use acoustic waves (eg. ultrasound imaging). However, acoustic imagine suffers from lack of spatial resolution due to the large divergence of acoustic waves.

A further known method of imaging comprises forming an image of an object from interference of two beams of coherent light, one of which has been scattered from a target (ie. holographic imaging). Holograms have been used to analyse non-visible parameters of a target, for example, vibration of an engine block. Holographic imaging suffers from several disadvantages Firstly, holograms require two investigative beams that must interfere and be coherent over the distance to the target. Secondly, holograms are not suited to imaging through opaque media. An image cannot therefore be produced at a distance greater than a single photon transport path of the light used to obtain the hologram. Thirdly, holograms arc unsuited for measurement through media that exhibit dynamic scattering, and the scattering will reduce the quality of images obtained.

Several known imaging techniques exist where an investigative wave is perturbed as it passes, scatters, reflects or is absorbed by a target. These techniques require that the form of energy used for the investigative wave, and its frequency, must be chosen to interact with the target and cannot thus be fully optimised for detection (i.e. low absorption an/or high spatial resolution and/or high signal to noise).

BRIEF SUMMARY OF THE INVENTION

It is an object of the present invention to overcome or substantially mitigate the above disadvantages.

According to a first aspect of the present invention there is provided a method of detecting an object located within a dynamic scattering media, the method composing:

i) directing a continuous coherent light wave of predetermined wavelength into the media;

ii) detecting dynamically scattered light emerging from the media;

iii) correlating the detected light photons in the time or frequency domain;

iv) determining the presence of an object from analysis of differences between said correlation and the correlation which would arise from photons scattered by the media only; and v) determining the approximate position of the object within the media from said analysis of the correlation and knowledge of the mean transport path of the light wave of predetermined wavelength within the media.

The term "light wave" is not limited to visible light but is to be interpreted as encompassing electromagnetic radiation of any suitable wavelength.

The media may be a turbid media of relatively high density and the object may be more or less dense and more or less viscous than the media. The object may be an object which absorbs and/or reflects the incident light waves.

The invention (from hereon referred to as Diffuse Wave Imaging) incorporates aspects of the known technique of Diffusing Wave Spectroscopy (DWS). DWS is used for sub-micron particle sizing and bulk rheology measurements in dense suspensions or emulsions. DWS is not applicable to the imaging of single objects within turbid media. Furthermore, DWS is not used to identify individual particles. The suppression of photons close to the axis of the auto-correlation traces is treated as a limitation of DWS. The inventors have realised that this suppression of photons which have undergone multiple scattering events can be used to determine the presence of an object, and by taking many measurements, to form an image.

The invention allows images to be obtained using photons which have travelled optical distances greater than 2 photon transport paths. This is opposite to conventional imaging of dense media, which generally removes or filters out light which has been scattered more than once. Since the invention does not require photons which have undergone ballistic and low order scattering, it is suitable for imaging very dense suspensions where ballistic scattering is limited.

The steps (i) to (v) may be iterated either sequentially or simultaneously using coherent light waves of different predetermined frequencies having different mean transport paths within the dynamic scattering media, to thereby obtain further information as to the approximate position of the detected object from the analysis of the respective correlations and knowledge of the respective mean transport paths. For instance, light of three different wavelengths may be used.

The or each iteration of steps (i) to (v) may be repeated, either sequentially or simultaneously, for additional locations within the media, the results then being combined to construct an image of the object within the media. Where only one wavelength of light is used the image will be two dimensional. However, using two or more different wavelengths as mentioned above (which effectively probe into different depths of the media and/or object, enables the construction of a, three dimensional image.

The light emerging from the media may be detected at one or more predetermined scattering angles, preferably a scattering angle of 180° and/or 0°.

The media may be modulated to induce, or enhance, dynamic motion within the media to provide or enhance the required dynamic scattering. Similarly, when the object is an object which is at least partially reflective of the or each light wave, the object may be modulated to enhance phase chances in light reflected therefrom.

The method may included the step of selecting for detection light which has a predetermined component of polarisation. The selection may be accomplished using polarising filters or fibre optic cables which preserve only one particular component of polarisation.

The or each light wave may be passed through a window prior to entering the media, the window being arranged to reflect light which is detected together with light emerging from the media, thereby producing a heterodyne signal. The window may be adjustably displaced relative to the origin of said light wave to allow control of the intensity of the reflected light which is detected. The window may be arranged to cause the reflected light to undergo multiple reflections before being detected, thereby enabling the path length travelled by the reflected light to be controlled.

The method may be performed on a human or animal body to detect the presence and approximate positions, or construct an image of a pathological entity within the body.

According to a second aspect of the present invention there is provided a method of detecting the presence of a pathological entity within the human or animal body, the method comprising:

i) directing a continuous coherent light wave of a first predetermined wavelength into the body;

ii) detecting dynamically scattered light emerging from the body;

iii) correlating the detected light photons in the time or frequency domain; and iv) determining the presence of a pathological entity from analysis of differences between correlation and the correlation arising from photons scattered by the media surrounding the entity only.

According to a third aspect of the present invention there is provided apparatus for detecting an object located within a dynamic scattering media, the apparatus comprising means for directing a continuous coherent light wave of a predetermined wavelength into the media, means for detecting dynamically scattered light emerging from the media, means for correlating the detected light photons in the time or frequency domain, whereby the presence of an object can be determined from analysis of differences between said correlation and the correlation which would arise from photons scattered by the media only, the approximate position of the object within the media can be determined from said analysis of the correlation and knowledge of the mean transport path of the light wave of predetermined wavelength within the media.

A plurality of detectors may be arranged in an array to provide a series of measurements simultaneously. The array of detectors may be coupled to 3 CCD camera.

Preferably the or each detector is either located adjacent the emitter or is displaced from the emitter and is located on the axis of emission of the emitter The coherent light producing means produces both visible light and infrared light.

Polarising filters may be located in front of the detection means to select either light with a polarisation perpendicular to the light emitted from the emitter, or to select light with the same polarisation as the light emitted from the emitter.

An object located within a medium may be caused to modulate to increase the contrast of the phase of scattered light, and thereby improve the resolution of the image.

The invention may be used in combination with Time of Flight apparatus to provide imaging over both short and long distances.

Where heterodyne detection is to be used, the coupling means may be provided with a window which will reflect a fraction of the light towards the detection means, thereby providing a heterodyne signal.

The window may be adjustably displaced from the coupling means to allow control of the intensity of reflected light incident at the detection means.

The window may be arranged to cause the reflected light to undergo multiple reflections before being incident at the detection means, thereby allowing the path length traveled by the reflected light to be controlled.

The coupling means and detection means may comprised polarisation preserving optical fibres. The fibres may be mounted so as to be rotatable through 90 degrees, thereby allowing modification of the effective numerical aperture of the fibres.

Preferably the means for producing coherent light comprises a laser.

Preferably four lasers operable at a different wavelength are used concurrently.

Preferably, two of the lasers are arranged to produce orthogonally polarised light, and a polarising beamsplitter cube is provided to couple the light into a polarisation preserving optical fibre.

The coupling means and detection means may comprise optical fibres with terminations located in a probe comprising a cylindrical head.

According to a fourth aspect of the present invention there is provided apparatus for detecting the presence of a pathological entity within the human or animal body, the apparatus comprising means for directing a continuous coherent light wave of a first predetermined wavelength into the body, means for detecting dynamically scattered light emerging form the body, and means for correlating the detected light photons in the time or frequency domain, whereby determining the presence of a pathological entity may be determined from analysis of differences between said correlation and the correlation arising from photons scattered by the media surrounding the entity only.

According to a fifth aspect of the present invention there is provided a method of detecting the presence of an object within a media, the method comprising i) inducing vibration in the object at a predetermined frequency which does not propagate efficiently within the media;

ii) generating a continuous coherent light wave;

iii) modulating the generated light wave at a second predetermined frequency;

iv) directing the modulated coherent light wave into the media;

v) detecting scattered light emerging from the media;

vi) analysing the detected scattered light for the existence of a beat signal corresponding to the beat frequency between the first and second predetermined frequencies thereby indicating the presence of the object.

The frequency of the induced vibration is selected to correspond To the resonant frequency of the object, or regions within the object to be detected. Such regions may for instance be regions of stress, such as cracks in the object.

The vibrating frequency may be varied until the object, or parts of the object to be detected, resonates, and wherein the size of the resonating object, or region of the object, is determined as a function of the resonating frequency.

An image of the object, or parts of regions of the object to be detected, may be constructed by detecting light scattered from different parts of the object.

The method may be performed on a human or animal body to detect the presence, or construct an image, of a pathological entity within the body.

The invention also provides apparatus for detecting the presence of an object within a media, the apparatus comprising:

i) means for inducing vibration in the object at a predetermined frequency which does not propagate efficiently within the media;

ii) means for generating a continuous coherent light wave;

iii) modulating the generated light wave at a second predetermined frequency;

iv) means for directing thy modulated coherent light wave into the media;

v) means for,detecting scattered light emerging from the media;

vi) means for analysing the detected scattered light for the existence of a beat signal corresponding to the beat frequency between the first and second predetermined frequencies thereby indicating the presence of the object.

The method and apparatus according to the fifth aspect of the invention may be used to investigate properties that cannot be imaged directly such as scaling in an oil pipe or cracks in a metal structure.

The modulation frequency may be used to perform a secondary function on the object. For example, resonance may be used to cause descaling of a pipe whilst an image (by means of measurement of the change in the magnitude of resonance at a single frequency or preferably the change in the resonant frequency) is used to monitor the descaling operation in real time. Similarly, where the methods is used on a human or animal body, the same method may be used to remove or destroy pathological entities such as tumours (wherein the resonance may heat and kill the target), gall stone (wherein the resonance will physically break down the target), kidney stones, and other growths, foreign bodies and abnormalities. A similar method may be used to remove blockages etc. in non-medical applications, such as to remove blockages from target objects such as underwater pipe lines or cables.

Resonance may also be used to modify the target object means of chemical release or activation.

The invention may utilise a naturally occurring source as the source of the investigative wave.

The present invention may be combined with existing detection or imaging systems, such as time of flight systems, CAT, electron resonance etc.

Other possible features of the invention will become apparent from the description below.

BRIEF DESCRIPTION OF THE DRAWINGS

Specific embodiments of the invention will now be described, by way of example only, with reference to the accompanying drawings, in which.

DETAILED DESCRIPTION OF EXEMPLARY EMBODIMENTS

Figure 1:
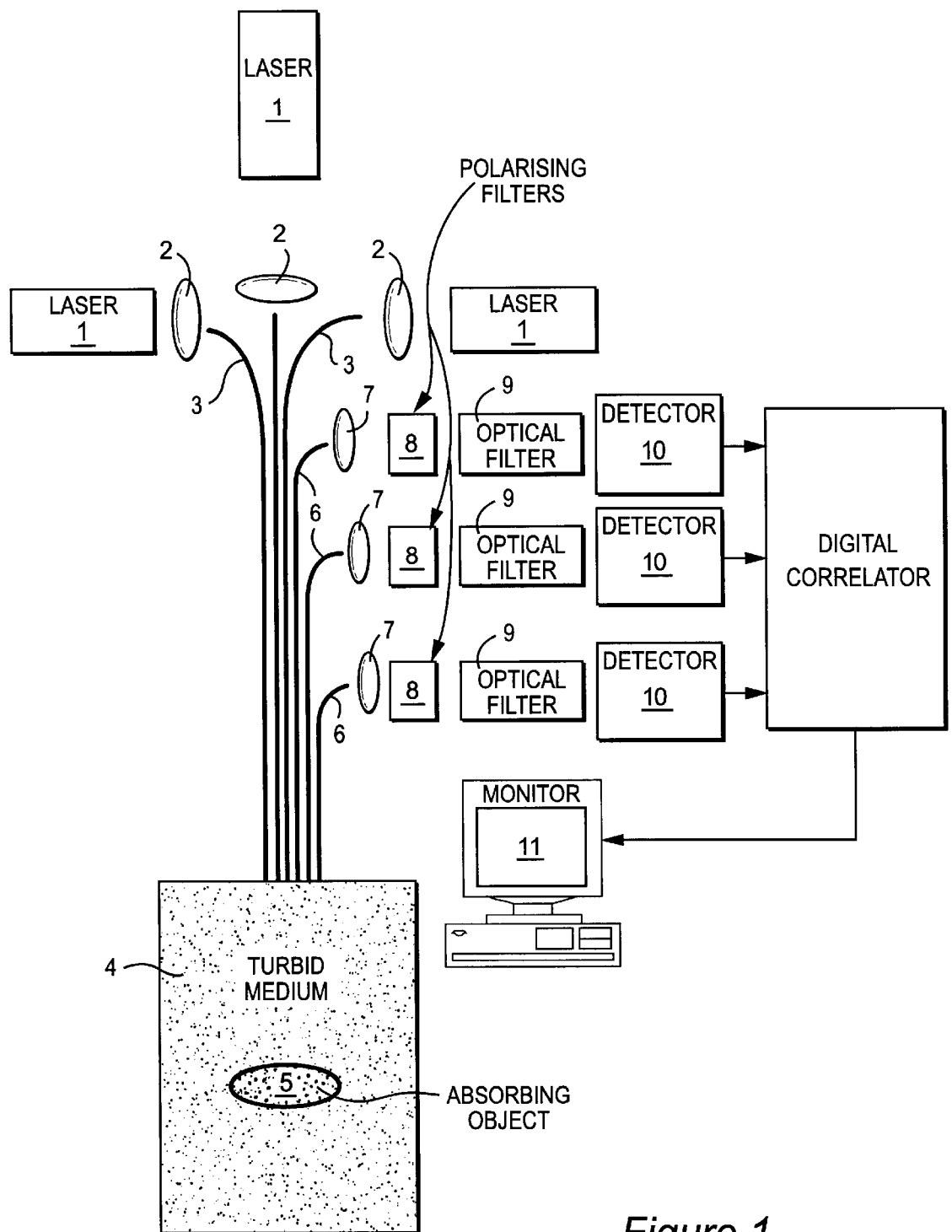
FIG. 1 is a schematic diagram of an imaging apparatus according to a first aspect of the present invention.

FIG. 1 shows an imaging apparatus comprising three lasers 1 operating at different wavelengths. The three lasers produce light wavelengths 488 nm (argon ion), 633 nm (helium neon) and 1064 nm (Nd:YAG) respectively, the light from each laser 1 having a single transverse and longitudinal mode. Optics 2 (an example of which is described in more detail below with reference to FIG. 6) couple light from each laser 1 into a single mode polarisation maintaining optical fibre 3. Light from each fibre 3 is launched into a turbid medium 4 within which is located an absorbing object 5.

Light scattered by the turbid medium 4 is collected by three optical fibres 6 which may have the same construction as the launch fibres 3. The collected light is collimated using farther optics 7 (an example of which is described in more detail below with reference to FIG. 7) and directed at polarising filters 8 and laser-line optical filters 9. Light transmitted by the laser-line filters 9 is monitored by detectors 10, a respective detector 10 being arranged to detect scattered light of each of the three laser 1 wavelengths. The detectors 10 are photon counting photon multiplier tubes or photon counting avalanche photodiodes, whichever is appropriate for the wavelength of light to be detected. An output it signal from each detector 10 passes to a digital correlator which produces a correlation trace (described below with reference to FIG. 2). The correlation trace may be displayed on a monitor 11.

The illustrated apparatus is configured to detect light scattered through 180degrees (back scatter). The apparatus could be configured to detect light scattered through other angles including light which, although scattered, exits the turbid medium 4 in the same direction as the incident light (i.e. scattering through 0 degrees). Whilst operation of the apparatus at any angle is possible, the mathematical modelling required to obtain imaging becomes more complicated for scattering angles other than 180 degrees or 0 degrees and thus these two configurations are preferred.

Figure 2A:
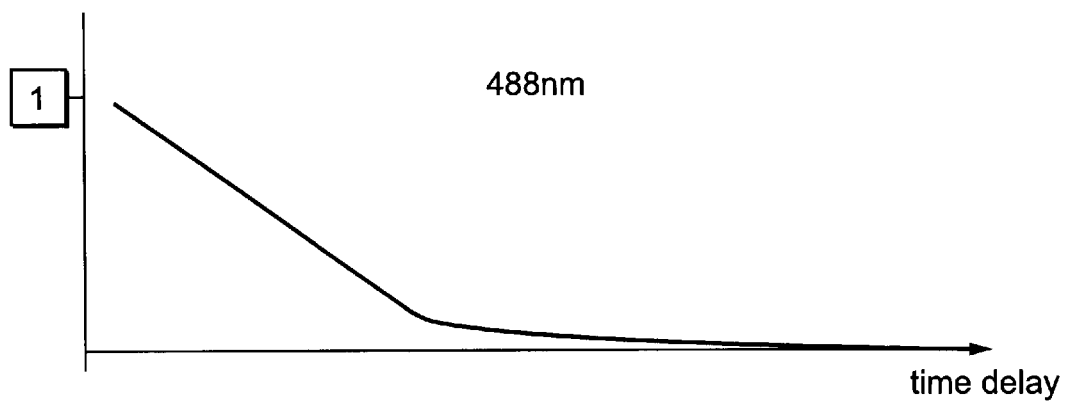
FIG. 2 is shows three auto-correlation traces which illustrate the operation of the apparatus of FIG. 1.
Figure 2B:
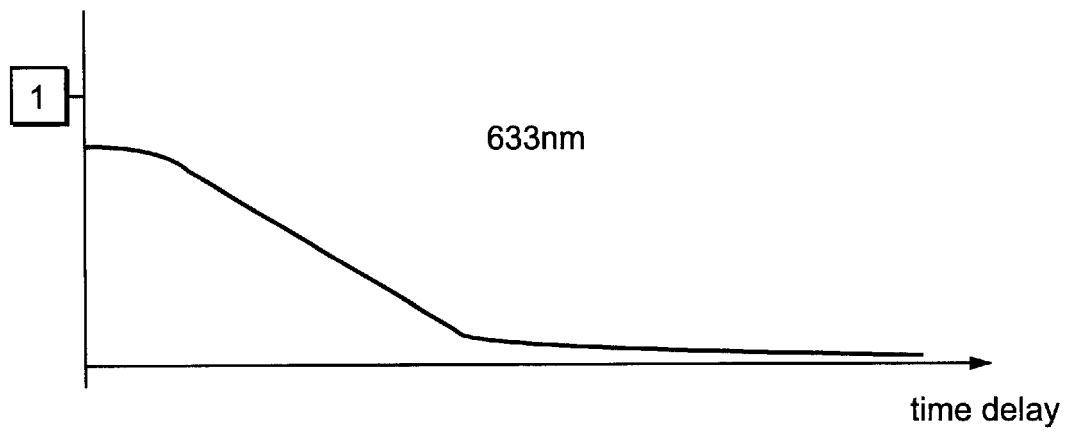
Figure 2C:
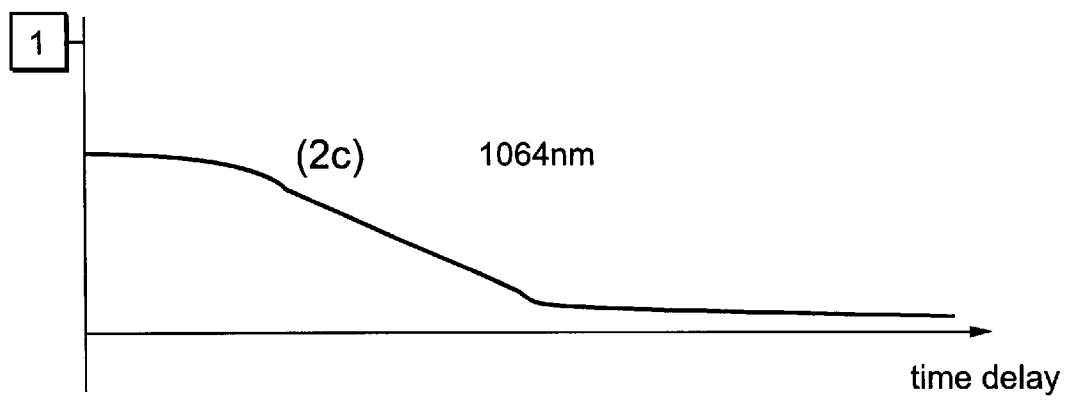

FIG. 2, parts 2a to 2c show three correlation traces obtained from the scattered light detected at each of the detectors 10. Each correlation is obtained by correlating detected light with itself (i.e. the known technique of autocorrelation). Each correlation trace shows the logarithm of the number of photons detected (vertical axis) versus the square root of the correlator delay time (i.e. the delay time of the auto-correlation of the detected signal). The region of the correlation trace near to the vertical axis represents photons which have undergone a great deal of scattering, lesser amounts of scattering are indicated further from the vertical axis (for light with purely random phase the correlation would be a flat line). It is important to note that some form of motion of the medium 4 is required so that scattering of the light by the medium will modify the phase of the light (Brownian Motion is often sufficient for this purpose).

The correlation trace of FIG. 2a is obtained from detection of the shortest wavelength light (i,e. 488 nm). The turbid medium 4 will scatter the relatively short wavelength light efficiently, and consequently in the illustrated example the average penetration of photons into the turbid medium 4 is less than the distance to the absorbing object 5. Thus, the short wavelength light is largely unaffected by the absorbing object 5, and the correlation trace obtained will have a shape characteristic of random scattering by the medium 4 (i.e. a straight line sloping downwardly away from a maximum value of 1). Thus the correlation trace indicates that the depth of the object 5 within the medium 4 is greater than the average scattering depth of the 488 nm light (the average scattering depth or 488 nm light in a given medium may be known from a reference text or from experimentation).

The correlation trace 2b is obtained from detection of the medium wavelength light (i.e. 633 nm), which has a greater average penetration depth than the relatively shorter wavelength light. The trace shows some attenuation close to the origin, which indicates that those photons which lave travelled the longest path through the medium 4 (approximating to diffuse photons) have been preferentially depleted by the absorbing object 5. Further away from the origin of the trace those photons which have travelled a shorter path are unaffected by the object 5, and the downward sloping straight line of the trace is unaffected by the shape of the correlation trace thus provides information pertaining to the depth and shape of the object 5.

Correlation trace 2c represents long wavelength light (i.e. 1064 nm) which has a greater average scattering depth than the 633 nm light. The effect of the object 5 on the trace is more accentuated than the effect on correlation trace B, since more of the 1064 nm photons penetrate sufficiently far into the medium 4 that many of them are absorbed by the object 5). Thus the shape of the correlation trace 2c provides further information pertaining to the depth and shape of the object 5.

The invention thus uses light of three different wavelengths to determine the position of the absorbing object 5. The depth of the object is determined by comparison of the shapes of the three correlation traces 2a–c.

A single measurement as described above will describe the position of a small area of the object 5. To obtain an image of the object the position of the optics (not shown) which launch light from the fibres 3 into the medium, and/or the position of the optics (not shown) which couple light from the medium into the fibres 6, are translated between measurements to provide a grid arrangement of measured areas.

The wavelengths used may be preselected to provide a desired range of penetration depths into a given medium. It is noted that a coherent light source capable of being tuned over a wire range of wavelengths (for example an Optical Parametric Oscillator) would provide the capability to pre-select wavelengths, and also to obtain many measurements at different wavelengths (although the three wavelengths used above should be sufficient to obtain accurate imaging).

The apparatus may comprise single emitters and multiple detectors, thereby allowing many point measurements. The fibres collecting scattered light could be coupled directly (or via an intensifier) to arrays of detectors such as charge-couple device (CCD) cameras.

Inclusion of the polarising filters 8 enables further resolution of the depth of the object 5. When polarising filters 8 are set so as to transmit light which is polarised transverse to the light from the lasers 1, only photons which have undergone many scattering events will be detected. This orientation of polarising filters thus suppresses detection of photons which have penetrated a relatively small distance into the medium 4. When the polarising filters 8 are rotated to transmit light which has the same polarisation as the light from the lasers 1, photons which have undergone many scattering events arc suppressed, and photons which have penetrated a relatively small distance into the medium 4 are detected.

When optical fibres 3,6 which support only a single eigen-mode of light at an appropriate wavelength are used, the polarising filters 8 are not needed. This is because the transverse polarisation of the light produced by the lasers 1 will be preserved by the fibres 3 which launch the light into the medium 4. The orientation of the fibres 6 which couple scattered light from the medium can be set so as to couple light with the same polarisation as that emitted from the lasers 1, or light with polarisation orthogonal to that emitted from the lasers. This will allow discrimination of penetration depth as described above.

Optical fibres 3,6 capable of supporting multiple wavelengths would reduce the number of fibres 3,6 required by the apparatus (it is noted that the use of polarisation maintaining beamsplitters would be advantageous in this arrangement to allow the combination of beams from the different lasers 1).

A fibre having multiple cores would allow different emitter/detector spacing within that fibre.

It is noted that the invention may be used to image reflecting objects, in addition to imagine absorbing objects as described above. Light reflected from the object will cause a perturbation at or close to the vertical axis of a trace.

The invention may be applied to imaging of the human body, for example to detect tumours. For body imaging, utilisation of both 180 and 0 degree measurements in a number of positions will produce the best results. The position of launch of light into the body or of collection of scattered light, may be varied by scanning the apparatus appropriately or by using multiple emitters and/or detectors. After operating the apparatus at a series of positions correlations obtained are normalised and compared. Differences in correlation functions close to the vertical axis will suggest a change in the effective 'viscosity' or 'refractive index' of the body at that point, which may indicate the presence of for example, a tumour.

Figure 3:
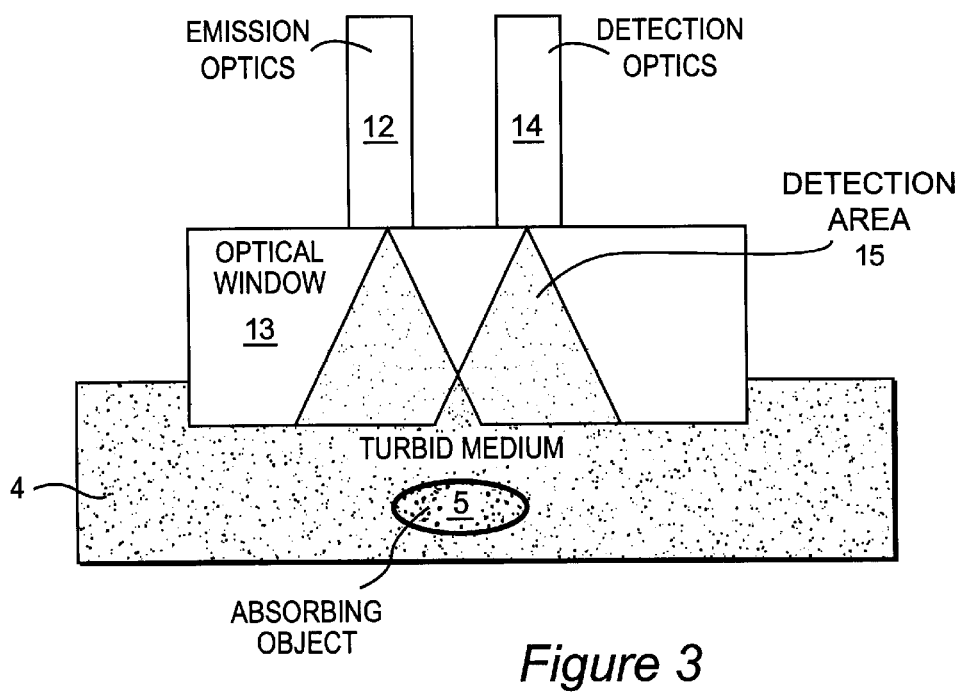
FIG. 3 is a schematic diagram of a first heterodyne window suitable for use with the present invention.

Heterodyne signal processing may be used prior to auto-correlation. An apparatus which will provide a heterodyne signal is shown in FIG. 3. Light is transmitted through emission optics 12 into a window 13. At a lowermost surface of the window 13 the light passes into the turbid medium 4, and a fraction of the light is reflected due to the difference in refractive index of the window 13 and the medium 4. Detection optics 14 collect scattered light and reflected light which interferes to produce a beat signal, and the beat signal is processed to provide imaging in the same way as described in relation to FIG. 2. The triangular area 15 located beneath the detection optics 14 represents the detection area of the optics 14 (i.e. corresponds to the numerical aperture of the optics 14). The emission optics 12 and detection optics 14 are index-matched to the window 13 to prevent waveguiding of light within the Window 13.

The apparatus shown in FIG. 3 has two limitations. The first limitation is that the ratio of heterodyne (i.e. reflected) light relative to scattered (i.e. homodyne) tight cannot be controlled. The second limitation is that the heterodyne light and homodyne light travel different path lengths, as a consequence of which stringent coherence of the beam is required. These two limitations are linked, since when the homodyne light has a short path length in the medium 4 the intensity of scattered homodyne light detected will be high and a strong heterodyne signal will be required.

Figure 4:
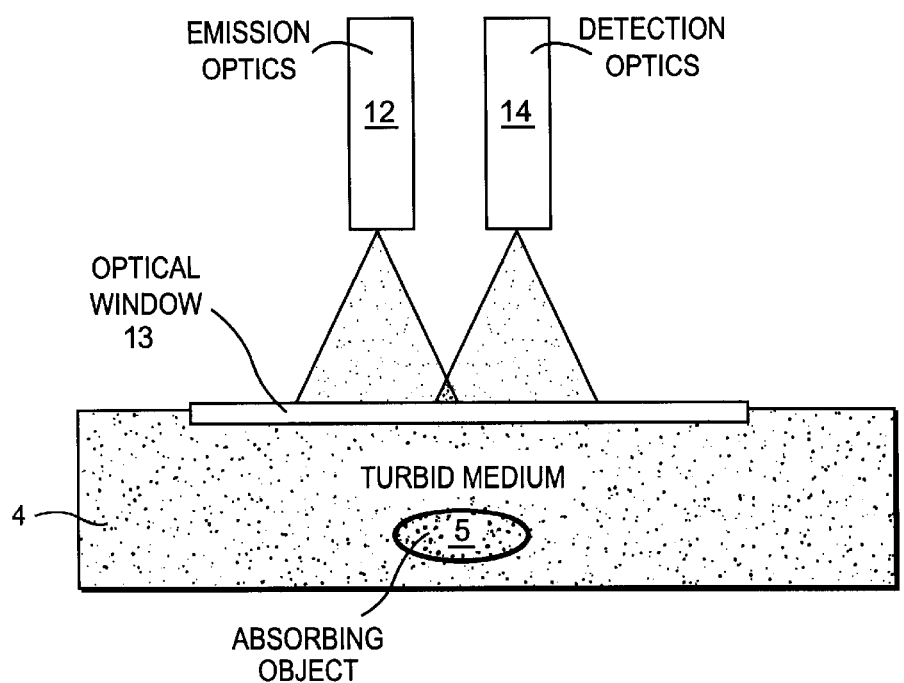
FIG. 4 is a schematic diagram of a second heterodyne window suitable for use with the invention.

An apparatus which overcomes the first of the above limitations is shown in FIG. 4. Emission optics 12 and detection optics 14 are located above optical window 13. The optics 12,14 are not index-matched to the window 13, and a proportion of light emitted from the optics 12 will be reflected by the window 13 and collected by the detection optics 14. The window is index-matched to the turbid medium 4 so that there are no reflections from the lowermost surface of the window 13. Light scattered by the medium 4 interferes with light reflected from the window 13 to provide a beat signal for professing as before. However, the separation of the window 13 from the optics 12,14 allows the optics to be moved relative to the window 13, thereby controlling the proportion of reflected light which is collected by the detection optics 14 (i.e. moving the window 13 further from the optics 12,14 will increase the proportion of reflected light collected).

Figure 5:
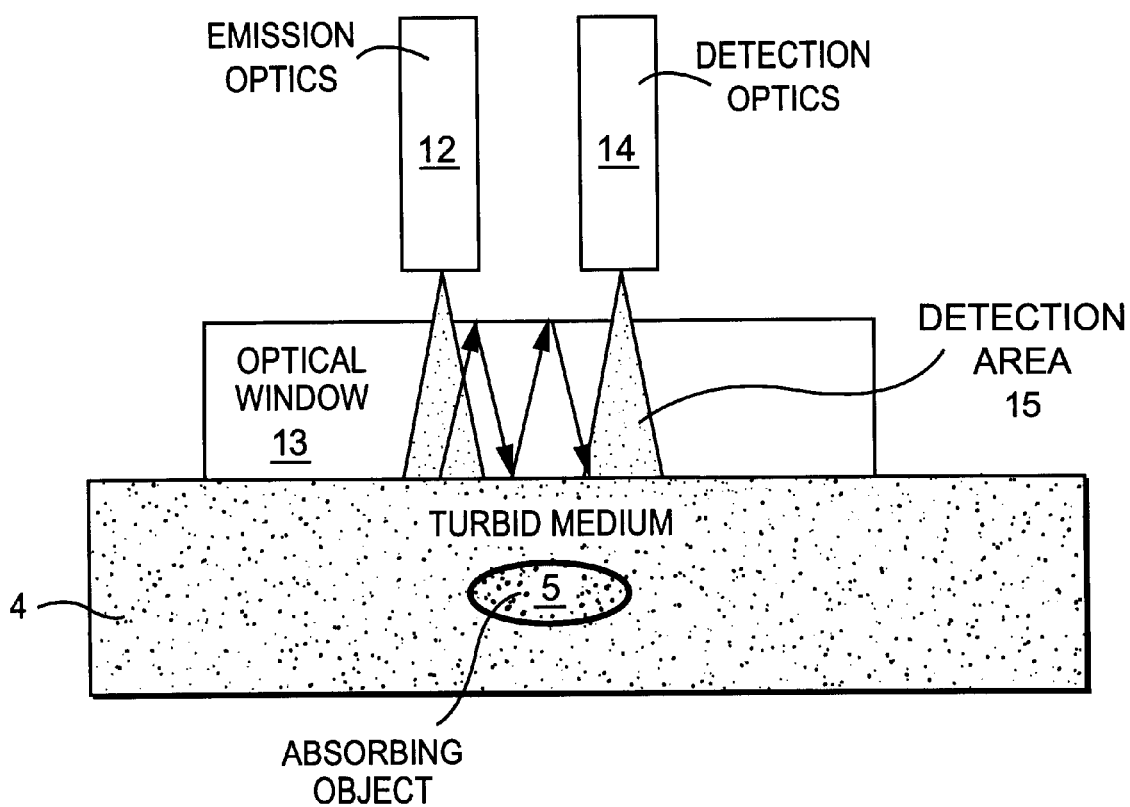
FIG. 5 is a schematic diagram of a third heterodyne window suitable for use with to the invention.

The apparatus illustrated in FIG. 4 does not allow control of the heterodyne path length (i.e. path length of the reflected signal). The mean path length of the heterodyne signal may be controlled using the window 13 as a guide for multiple reflections as shown in FIG. 5. The emission optics 12 and detection optics 14 are not index-matched to the window 13, and the window is not index-matched to the turbid medium 4, so that a portions of the emitted light is reflected from the uppermost and that lowermost surfaces of the window 13. Heterodyne light may enter the detection area (4) by multiple reflections from the surfaces of the window 13. Moving the window 13 toward the emission optics 12 and the detection optics 14 will reduce the heterodyne signal, and increase the mean optical path length of the heterodyne signal. Reduction of the path length of the heterodyne component (by moving the window 13 further from the probe) will increase the heterodyne signal strength. Thus, using a windows 13 of selected material, optical coatings and thickness it is possible to provide a heterodyne signal of the desired path length and intensity.

It is noted that since light will be emitted by the emission optics with a finite divergence, there will be a spread in the path lengths travelled by the heterodyne light.

Figure 6:
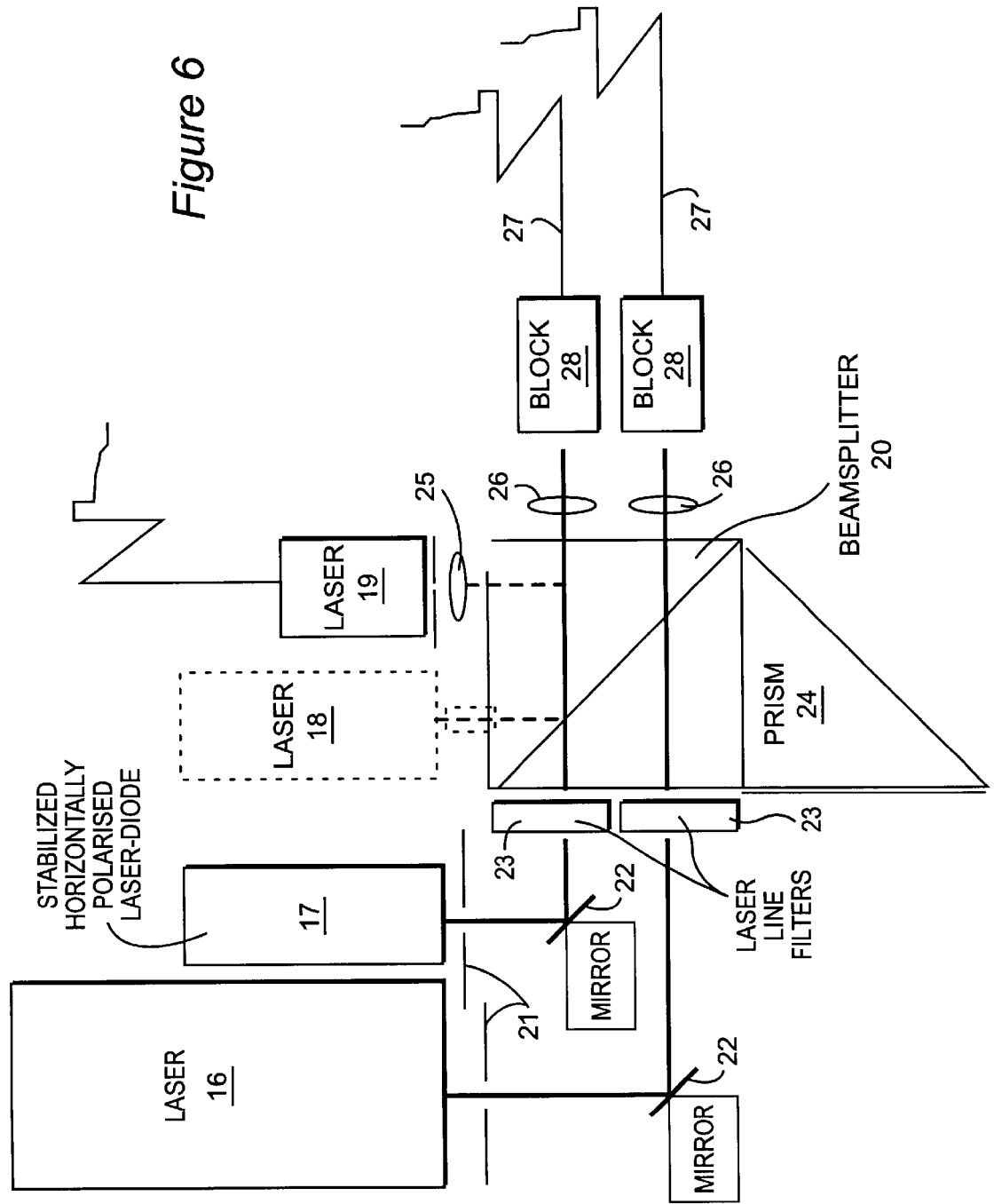
FIG. 6 is a schematic diagram of a light generating apparatus.

FIG. 6 illustrates a configuration for coupling light from several lasers into two optical fibres. A configuration based on that illustrated may be used to couple light from three lasers into three separate optical fibres, as is required by the apparatus shown schematically in FIG. 1 and described above.

The primary lasers are: a single longitudinal mode frequency doubled horizontally polarised Nd:YAG laser 16 (5 mw of output power at 532 nm), and a stabilised horizontally polarised 675 nm laser-diode unit 17. Two further lasers may be used to provide light at wavelengths of 580–833 nm (eg. 780 nm stabilised diode laser 18) and 450–670 nm (eg. 488 nm single transverse mode argon ion laser 19).

Light from the Nd:YAG laser 16 and diode laser 17 is directed to a polarising beamsplitting cube 20 via baffles 21 and mirrors 22. The dimensions of the baffles 21 and mirrors 22 are minimised to reduce the possibility of multiple reflections of light re-entering the lasers 16,17. The mirrors 22 are capable of rotational and translational movement. Light from the lasers 16,17 may pass through laser line filters 23 (eg. birefringent filters) if required.

Since the light from the lasers 16,17 is horizontally polarised it will pass, without reflection, through the polarising beamsplitter cube 20. Any component of the light which is not horizontally polarised will be directed down to a prism 24. One short side of the prism 24 is painted black, to minimised reflection of the light back to the polarising beamsplitter cube 20.

The polarising beamsplitter cube 20 is used to combine (vertically polarised) light from the 488 nm laser 19 With the light from the Nd:YAG laser 16, and to combine (vertically polarised) light from the 780 nm stabilised diode laser 18 With light from the 675 nm laser-diode unit 17. Light from the 488 nm single transverse mode argon ion laser 19 is coupled to the beamsplitter cube 20 using a suitable lens 25. The lens 25 may for example be plano-convex, anti-reflection coated on a curved side and coupled to the polarising beamsplitter cube 20 to reduce reflections from the interface between the lens 25 and the polarising beamsplitter 20. The 780 nm laser 18 may be collimated via a gradient index lens which is index-matched to the beamsplitter cube 20.

The beams pass from the polarising beamsplitter cube 20 to two achromatic lenses 26 which focus the light into aligned fibres 27 held in two blocks 28.

Light at 532 nm from the Nd:YAG laser 16 is launched onto The fast axis of a first of the optical fibres 27a, and light from the 488 nm laser 19 is launched onto the slow axis of the first optical fibre 27a. Similarly, light from the 675 nm laser-diode unit 17 is launched onto the fast axis of a second of the optical fibres 27b, and light from the 780 nm stabilised diode laser 18 is launched onto the slow axis of the second optical fibre 27b. Using the slow axis of the fibre 27 (which has a high numerical aperture) for the shorter wavelength 488 nm light accentuates the increased scattering suffered by the lower wavelength, once the 488 nm light will have a wider angle close field of view compared with the 532 nm light. The 675 nm light is directly comparable with the 532 nm light since both pass down a fast axis of a fibre 27. However, the 675 nm light will suffer less scattering within a turbid medium and will thus analyse material weighted deeper in the sample.

The blocks 28 are capable of rotating the optical fibres 27 through 90 degrees to allow the eigenmodes of the fibres 27 to be changed. The part of the fibres 27 held in the blocks 23 is mode-stripped to prevent light being launched into the cladding of the fibres 27.

An avalanche photodiode may be used to detect the 780 nm light, the other wavelengths being detected using photo-multiplier tubes.

Coupling light into a medium using low numerical aperture optics, and detecting light polarised at right angles to the coupled light will allow objects as deep as possible to be detected, and ensures that only high order multiple scattering is detected, which scattering is most suited to the known multiple light scattering models. By altering the wavelength of the coupled light, the depth monitored by the technique will be significantly affected, since scattering or light is wavelength dependant. Where both transmission (0 degree scattering) and back-scatter (180 degree scattering) measurements are possible, information pertaining to the depth of an object in the medium could be obtained from the difference between these two measurements.

Figure 7:
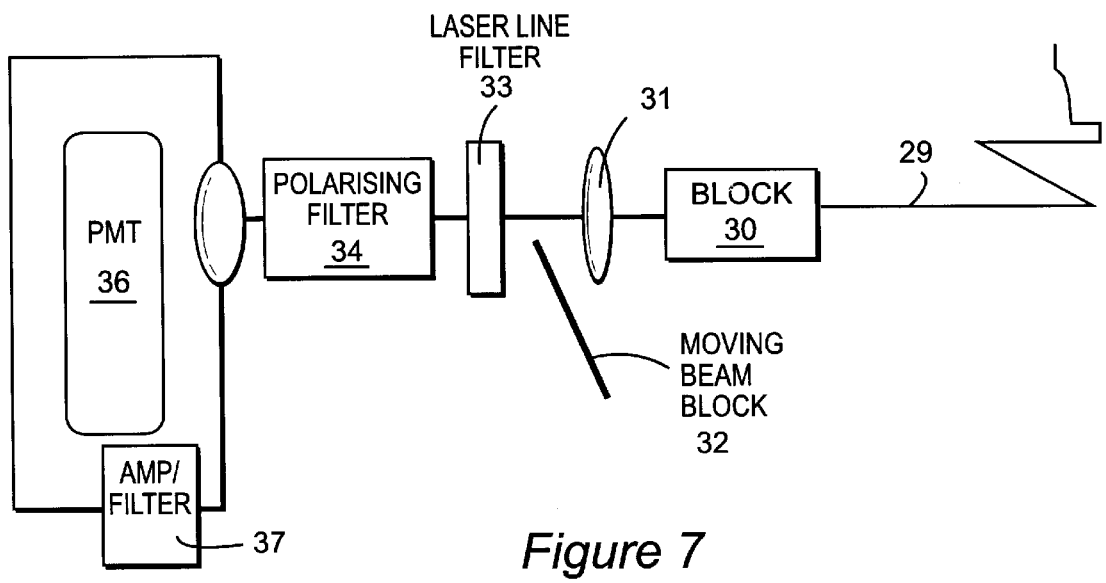
FIG. 7 is a schematic diagram of a detection apparatus.

FIG. 7 illustrates apparatus for detecting light scattered by a turbid medium, and may comprise part of the apparatus shown schematically in FIG. 1 and described above.

In the apparatus illustrated light is coupled by detection optics (not shown) into an optical fibre 29. An emission end of the fibre 29 is held in a block 30 that is fixed in one of two positions to allow selection of polarisation modes. An achromatic lens 31, of higher numerical aperture than the fibre to allow for misalignment, collimates light from the fibre 29. The light may be attenuated by a simple moving beam block 32; this is more efficient than attenuating or reducing the laser intensity since both the signal and the background are attenuated. The light passes through a laser line (or other) filter 33 which removes unwanted laser frequencies and background noise. A polarising filter 34 selects the required polarisation state, and the light is then focused by an achromatic lens 35 onto a photo-multiplier tube 36 (or avalanche photodiode). The signal detected by the photo-multiplier tube 36 is amplified and filtered 37 prior to signal analysis.

Figure 8B:
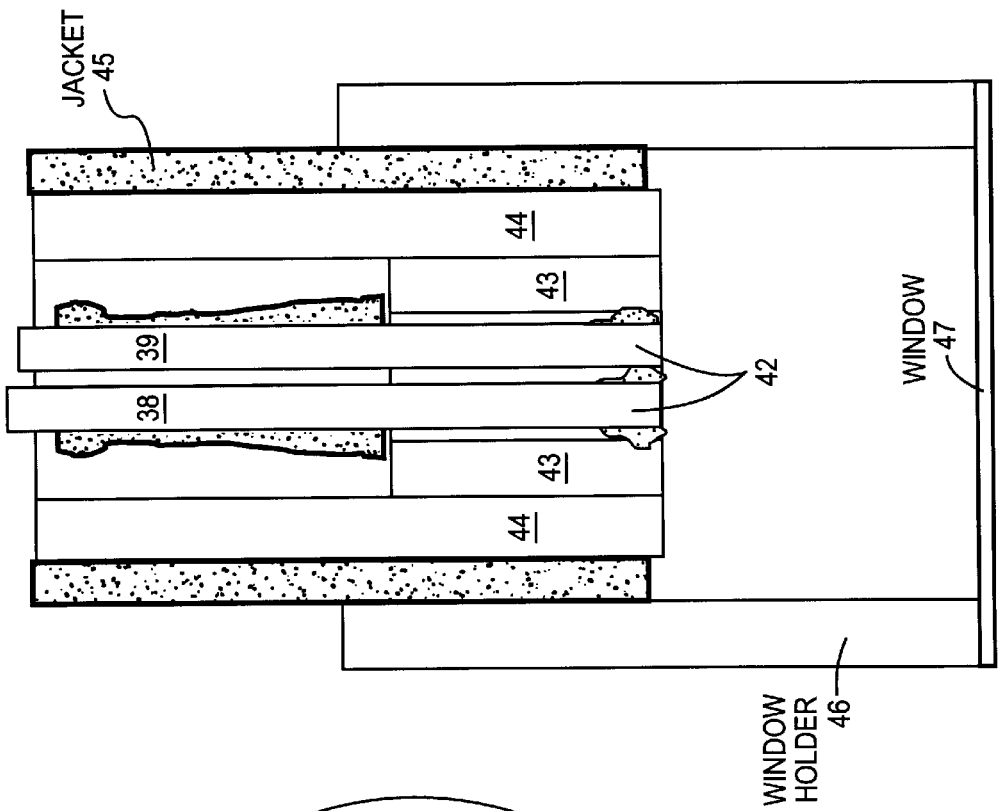
FIGS. 8a and 8b schematically diagram orthogonal cross-sections of a probe for use in the present invention.
Figure 8A:
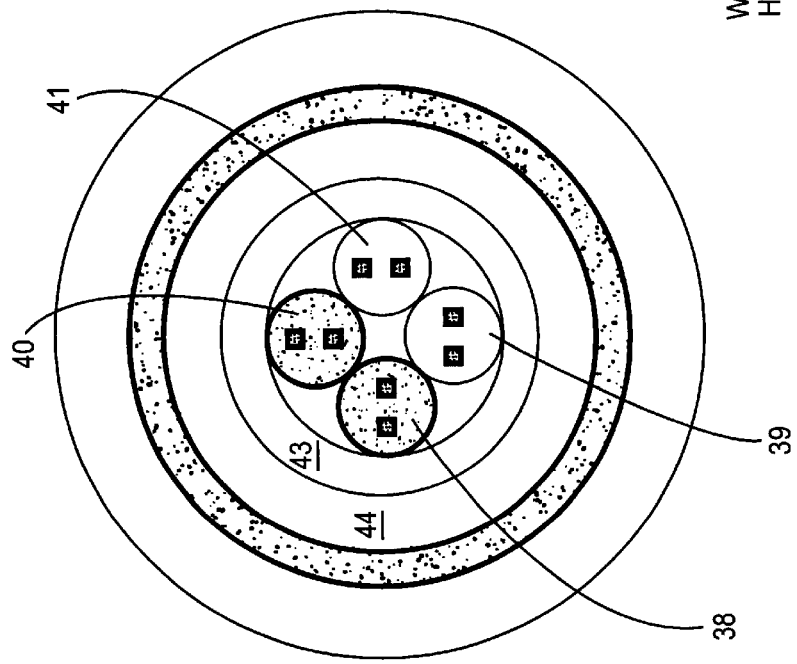

FIGS. 8a and 8b shows a fibre probe which combines emission fibres 38,39 and detection fibres 39,40. The fibre probe may be used as part of the apparatus shown schematically in FIG. 1 to couple light into and out of a turbid medium Light of 488 nm and 532 nm is emitted down a first fibre of the probe 38 and collected by a second fibre 40. Both fibres 38,40 are bow tie (polarisation preserving) fibres, their eigen modes being set at 90 degrees so that only light which has suffered a polarisation rotation through 90 degrees during scattering in the turbid medium will be detected. The 675 and 780 nm light is similarly emitted and detected by fibres 39,41. The fibres 38–41 are glued at their tips 42 into a short capillary 43, typically a few mm long. The tips 42 of the detection fibres 39,41, and an adjacent portion thereof, are stripped of fibre cladding, and black paint is applied around the outside of the fibre to mode-strip the collected light (i.e. prevent light being coupled into the cladding). The short capillary 43 is filled with black paint. The emission 38,40 and detection 39,41 fibres are held in separate jackets (not shown), beyond the capillary 43, to prevent cross talk of light between them.

A second capillary 44 surrounds the first capillary 43 and fibres 38–41 (typical diameter 3 mml, and further capillaries may be added. The second capillary 44 is encased to within 0.5 mm from the ends of the fibres 38–41 with a protective steel jacket 45. The jacket 45 is a loose sliding fit on the capillary 44 and is affixed with silicone, to stop thermal stressing. The probe is fitted with a window holder 46 that forms a close sliding fit with the steel jacket 45. A window 47 may be glued or fused to the holder 46. A temperature sensor (not shown) may be attached to the window holder 46.

Figure 9:
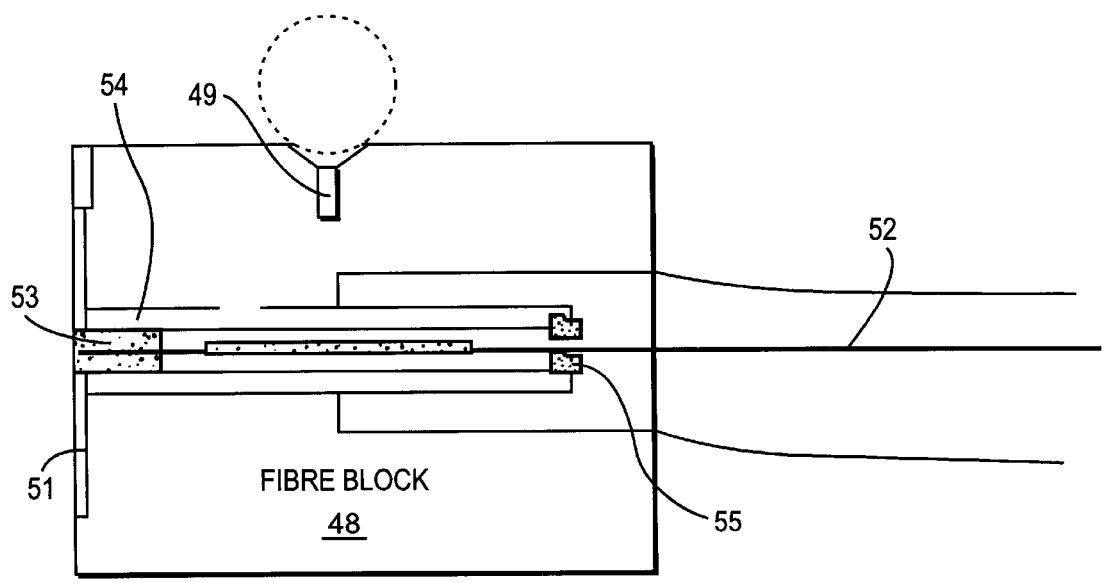
FIG. 9 is a schematic diagram of a fibre block for use in the present invention.

A fibre block of the type which has been shown in FIGS. 6 and 7 is illustrated in detail in FIG. 9. The fibre block 48 is cylindrical and is provided with two chamfered holes 49 spaced apart by 90 degrees about the block. A single ball bearing 50 provided in a block-mounting (not shown) is resiliantly biased to locate within either of the holes 49, thereby allowing the block to be rotated accurately through 90 degrees about its axis. The block 48 has a recessed face 51 to allow polishing of a fibre held therein 52 and an inner capillary 53 without contamination. The inner capillary 53 is located in an outer capillary 54 allowing that part of the fibre 52 which is mode-stripped to be protected. The fibre 52 is glued to the inner capillary 53 and supported by silicone 55 as it exits the outer capillary 55.

The area of a medium which is imaged by the apparatus described above will be influenced by the distance and angle between the detetor/s and emitter optics.

Auto-correlation of the detected signal, or heterodyne detection, may be substituted by any other processing which is sensitive to the dynamics of a system being imaged, for example pulse arrival distribution or a frequency scan from a etalon.

Where the object is reflective the object itself may be used to obtain a heterodyne signal.

The methods according to the present invention have been in terms of light of visible frequency, however any wave foam that may be produced with a coherence equivalent to the maximum path length difference of the quanta may be used.

The invention is applicable to any system where information is to be transmitted through turbid media, although it is particularly suited to body imaging and undersea surveillance.

For imaging of a reflective object, where insufficient dynamic information is present to obtain a useful correlation (due to in insufficient amount of Brownian Motion in the target), a modulator may be used to induce vibration of the object. Inducing resonance of an object will thus improve the contrast obtained via diffuse wave imaging (the resonance of the object will result in a heterodyne signal).

For imaging of an absorbing object, the vibration may be induced in the medium surrounding the object may be in the event that there is insufficient Brownian Motion to provide dynamic scattering of light in the medium.

A specific application of diffuse wave imaging in which resonant modulation of a target may be useful is imaging of the human body, for example where the body has a rumour growth, foreign body or other abnormality surrounded by normal tissue. A sonic wave may be used to set-up resonance of the target tissue without inducing significant modulation in the tissue surrounding the target. Tissue will give a very low frequency dynamic scattering signal (Brownian type motion) as particles in the tissue are constrained and scattering centres are located in a soft solid.

The resonance of the target tissue will depend upon its viscoelastic properties and size of the primary particles constituting the target. Diffuse Wave imaging apparatus may be used to view the target directly. Resonance of the target may also be used to treat the foreign body as it is being viewed, i.e. to break a gall stone, or to heat a tumour. Resonance may also be used to trigger a secondary (or more) chemical reaction such as a drug release whilst the target is imaged.

An alternative technique for obtaining an image of a modulating object which does not use Diffuse Wave Imaging will now be described with reference to FIGS. 10 and 11 (the technique will be referred to as Antenna Imaging). Antenna Imaging uses a modulation of an investigative wave (usually optical, and from hereon referred to as investigative beam) and modulation of a target by a modulation wave (usually acoustic). The frequency Of the modulation wave is chosen to be between 10 and 90% of the frequency applied to the investigative beam. Therefore, if the investigative beam has a frequency F. The modulation wave may have a frequency of 0.75F. A fraction of the investigative beam is diverted towards a detector, without first entering the medium, thereby providing a heterodyne beam.

The investigative beam will be scattered from the target, and a proportion of the investigative beam will also be scattered by the medium surrounding the target. Light from the investigative beam that has not been scattered from the target will have a modulations frequency F, although there will be a spread of modulation frequencies due to dynamic light scattering in the media. This light is combined with the heterodyne beam prior to detection to produce a beat signal, which in this case will have a frequency of 0Hz. Light that hits the target will have the modulation frequency of the target applied to it. When this light is combined with the heterodyne beam it will produce beats of frequency 0.25F (ie. F-0.75F), thus indicating the presence of the target.

The investigative beam and/or the modulation wave may be scanned (both spatially, or by frequency), thereby allowing an image to be built up. The wavelength and other physical properties (eg. polarisation) of the investigative wave and the detection means, may be used to alter the depth of penetration of the investigative wave into the media surrounding the target.

Where the media is absorbing of the investigative wave, and the absorption is a function of wavelength then a series of wavelengths may be used to analyse the depth of the target. Where the media is scattering and the scattering is a function of wavelength, this property may also be used to analyse depth of the target.

All returning light will have a slight frequency spread due to dynamic light scattering by the media. However, the detected signal is integrated between 0.1F and 0.4F before forming an image, thus lessening the effect of the frequency spread. Multiple scattering of the light (or other investigative wave) may lead to a slight loss of resolution, but since the invention uses the magnitude and position of the centre frequency of the detected light to form the image, dynamic scattering of the light will have only a limited effect.

Two forms of resonance modulation may be used to induce modulation of the target. The first form of modulation is modulation of the entire target, where the wavelength is a harmonic of the target. In this form the resonant frequency may be used to size the object very accurately. The second form of modulation is modulation of constituents of the target, where in primary particles within the target are made to modulate. The modulation could have a secondary function of heating or breaking down the target or objects attached to it.

The medium surrounding the object could be made to modulate whilst the object to be imaged is not modulated. For example, in imaging of the human or animal body it may be practical to choose an acoustic wavelength that passes through normal tissue but is highly attenuated by a tumour (in order to induce motion in the tissue, and thereby obtain dynamic light scattering). Correlation traces thus obtained will be of the same form as those shown FIG. 2, but with increased contrast.

In one specific example of an application of the invention, an undersea pipe may be modulated directly at an oil platform or a shore base, at a resonant frequency that does not propagate efficiently through water. An antenna camera may then be used to track the pipe and provide an image of the pipe. Alternatively, the pipe may be modulated by a transducer permanently located on the pipe.

The pipe may be imaged directly, for example to look for damage (ie. a source of light and detector may be located immediately adjacent the pipe). In this case a transducer may be included as part of a single piece of equipment which also contains the light source and detector.

Resonant modulation of the pipe may allow imaging of cracks, blockages and buildup within the pipe which would not otherwise be visible. This is done by choosing a modulation frequency which corresponds to a frequency of, for example, blockages located within the pipe. Sensitivity to a blockage may be improved by varying and measuring the resonant frequency at the blockage.

Figure 10:
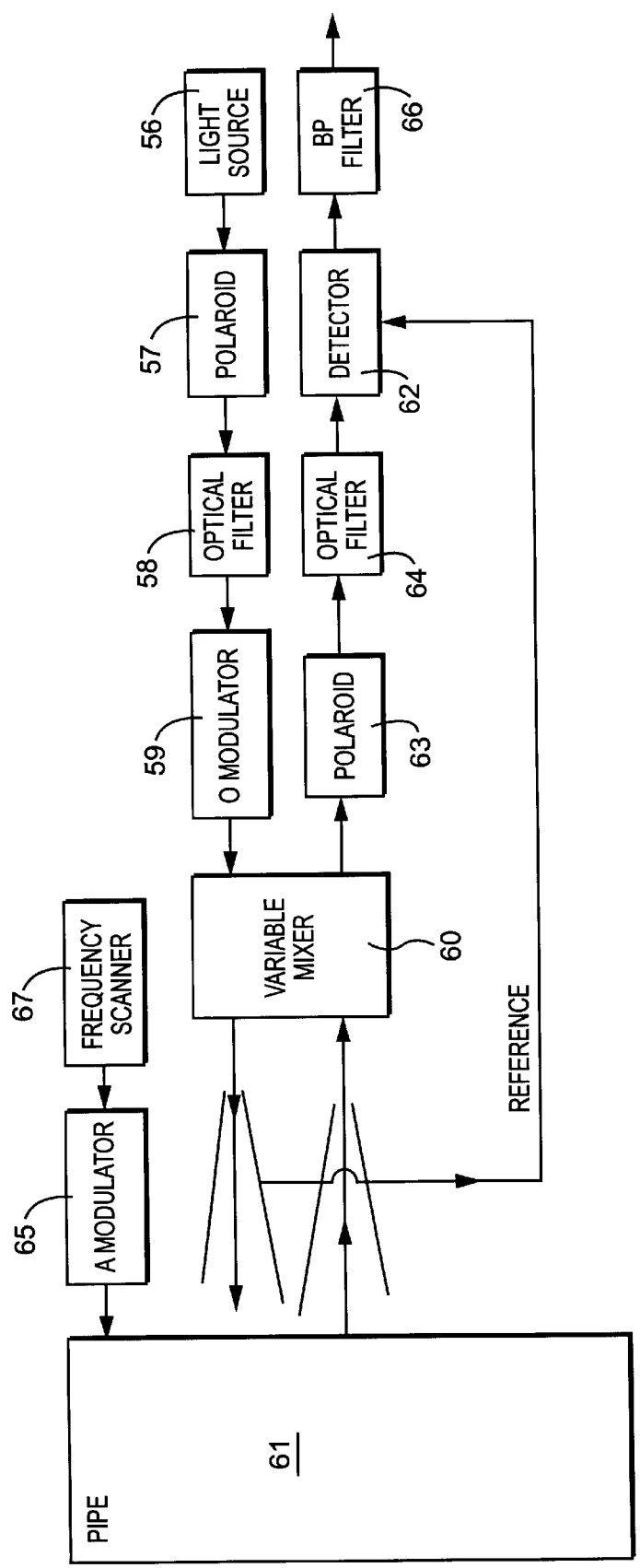
FIG. 10 is a schematic illustration of an imaging apparatus according to a second aspect of the invention.
Figure 11A:
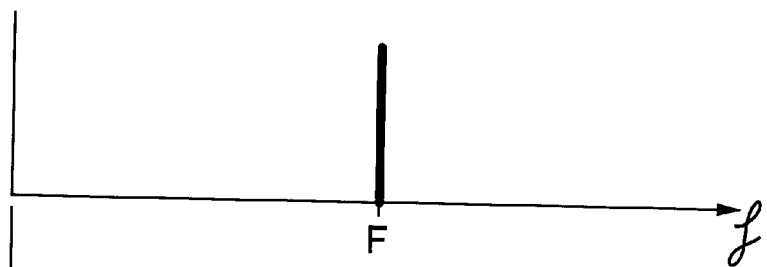
FIG. 11 is a schematic illustration of the operation of the apparatus of FIG. 10.
Figure 11B:
Figure 11C:
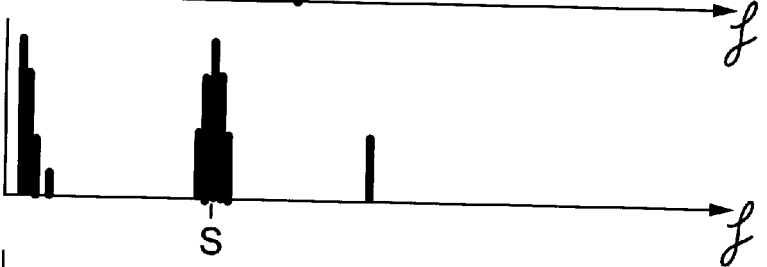
Figure 11D:
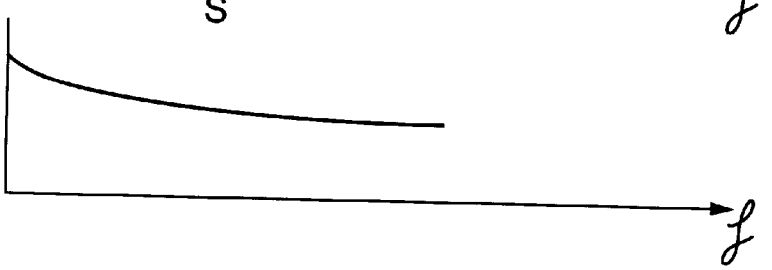

An apparatus which may be used to provide an image of a pipe located on the sea bed is shown in FIG. 10. A light source 56 emits coherent light which is coupled through a polarising filter 57 and an optical filter 53. The light is then modulated at a frequency F by an optical modulator 59, and passes via a variable mixer 60 into a medium in which the target 61 is located (in this example the medium is water, and the target 61 is a pipe).

A proportion of the coherent light is diverted towards a detector 62 without entering the water, and this light forms a reference. The remaining light is coupled into the water, and is scattered by the water and from the pipe 61. Scattered light is collected and passes through the variable mixer 60, via a polarising filter 63 and an optical filter 64 to the detector 62.

A modulator 63 is located on the pipe 61 and is used to cause resonant modulation of the pipe 61. This resonant modulation will be applied to the coherent light when it is scattered from the pipe 61. When scattered light is detected it will interfere with the reference light to produce a beat signal, with a frequency determined by the difference between the frequency of modulation of the pipe 61 and the frequency of modulation of the coherent light by the modulator 59. The generation of the beat signal is described above. A band-pass filter 66 is used to select the beat frequency from the signal produced by the detector 62.

The polarising filters 57, 63 are set at orthogonal polarisations when the apparatus is used to detect light that has travelled more than one photon transport path, or when the target is not a specular reflector, since this minimises detection of photons which have been scattered by the water rather than the pipe 61. When the apparatus is used in this way 50% of the light that has been scattered from the pipe 61 will be filtered out by the polarising filter 63. However, the suppression of photons which have undergone low order scattering in the water offsets this loss of signal. The optical filter 58 may be used in conjunction with a spatial filter (not shown) to improve the coherence of the light prior to modulation.

FIG. 11 illustrates the operation of the apparatus of FIG. 10. FIG. 11a shows the frequency F of the modulation applied to the coherent light by the modulator 4. FIG. 11b shows the frequency applied to the pipe 61 by the acoustic modulator 10. FIG. 11c shows the frequency spread of light incident at the detector 62. Light which has been scattered from the pipe 61 will have a frequency component labelled 'S'. There is significant broadening of the detected frequency about 'S' due to scattering of the light by the water. There will also be a significant noise band at 0Hz due to homodyne scattering of the light, and the line-width of this light will be broadened due to scattering. FIG. 11c shows a trace obtained by auto-correlation of the detected signal. The auto-correlation is used to provide imaging of the pipe.

Heterodyne imaging (i.e. where the investigative light is made to mix with light that has travelled a different path) does not necessarily require direct modulation of the investigative beam as described above. Heterodyning of the investigative beam could also occur between light modulated by the target and light scattered by the media, although this will limit control of the relative magnitude of the reference signal. Heterodyning of the investigative beam could also occur between light modulated by the target and a portion of light taken from the incident bean (conventional heterodyne). This gives a signal around 0Hz and is ideal for digital correlation of quanta but is noisy or signal analysers.

Apparatus for providing a heterodyne signal obtained directly from a source is illustrated in FIGS. 3 to 6 as described above.

What is claimed is:

1. A method of detecting an object located within a dynamic scattering media, the method comprising:

i) directing a continuous coherent light wave of predetermined wavelength into the media;

ii) detecting dynamically scattered light emerging from the media;

iii) auto-correlating the detected light photons in the time or frequency domain;

iv) determining the presence of an object from analysis of differences between said auto-correlation and the auto-correlation which would arise from photons scattered by the media only; and v) determining the approximate position of the object within the media from said analysis of the auto-correlation and knowledge of the mean transport path of the light wave of predetermined wavelength within the media.

2. A method according to claim 1, wherein steps (i) to (v) are iterated either sequentially or simultaneously using coherent light waves of different predetermined frequencies having different means transport paths within the dynamic scattering media, to thereby obtain further information as to the approximate position of the detected object from the analysis of the respective auto-correlations and knowledge of the respective mean transport paths.

3. A method according to claim 1, wherein the or each iteration of steps (i) to (v) is repeated, either sequentially or simultaneously, for additional locations within the media, the results then being combined to construct an image of the object within the media.

4. A method according to claim 1, wherein emerging light is detected at one or more determined scattering angles.

5. A method according to claim 4, wherein emerging light is detected at at least one scattering angle chosen from the group consisting of 180° and 0°.

6. A method according to claim 1, comprising selecting for detection light which has a predetermined component of polarisation.

7. A method according to claim 1 wherein the light wave is passed through a window prior to entering the media, the window being arranged to reflect light which is detected together with light emerging from the media, thereby producing a heterodyne signal.

8. A method according to claim 7, wherein said window may be adjustably displaced relative to the origin of said light wave to allow control of the intensity of the reflected light which is detected.

9. A method according to claim 7, wherein the window is arranged to cause the reflected light to undergo multiple reflections before being detected, thereby enabling the path length travelled by the reflected light to be controlled.

10. A method according to claim 1, performed on a human or animal body to detect the presence and approximate position, or construct an image, of a pathological entity within the body.

11. A method of detecting the presence of a pathological entity within the human or animal body, the method comprising:

i) directing a continuous coherent light wave of a first predetermined wavelength into the body;

ii) detecting dynamically scattered light emerging from the body;

iii) auto-correlating the detected light photons in the time or frequency domain; and iv) determining the presence of a pathological entity from analysis of differences between auto-correlation and the auto-correlation arising from photons scattered by the medial surrounding the entity only.

12. Apparatus for detecting an object located within a dynamic scattering media, the apparatus comprising:

means for directing a continuous coherent light wave of a predetermined wavelength into the media, means for detecting dynamically scattered light emerging from the media, means for auto-correlating the detected light photons in the time or frequency domain, whereby the presence of an object can be determined from analysis of differences between said auto-correlation and the auto-correlation which would arise from photons scattered by the media only, the approximate position of the object within the media can be determined from said analysis of the auto-correlation and knowledge of the mean transport path of the light wave of predetermined wavelength within the media.

13. Apparatus for detecting the presence of a pathological entity within the human or animal body, the apparatus comprising:

means for directing a continuous coherent light wave of a first predetermined wavelength into the body, means for detecting dynamically scattered light emerging from the body, and means for auto-correlating the detected light photons in the time or frequency domain, whereby determining the presence of a pathological entity may be determined from analysis of differences between said auto-correlation and the auto-correlation arising from photons scattered by the media surround the entity only.

* * * * *